United States Patent
Tani et al.

(10) Patent No.: US 6,432,978 B1
(45) Date of Patent: Aug. 13, 2002

(54) SF2809-I,II,III,IV,V AND VI SUBSTANCES EXHIBITING CHYMASE-INHIBITING ACTIVITIES

(75) Inventors: Masato Tani; Yasuhiro Gyobu; Chieko Moriyama; Toru Sasaki, all of Yokohama; Osami Takenouchi, Hino; Takashi Kawamura, Hino; Takashi Kamimura, Hino; Toshiaki Harada, Hino, all of (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/857,037
(22) PCT Filed: Dec. 1, 1999
(86) PCT No.: PCT/JP99/06738
§ 371 (c)(1),
(2), (4) Date: May 31, 2001
(87) PCT Pub. No.: WO00/32587
PCT Pub. Date: Jun. 8, 2000

(30) Foreign Application Priority Data

Dec. 1, 1998 (JP) ............................................ 10-341523

(51) Int. Cl.[7] ........................ C07D 401/06; A61K 31/47
(52) U.S. Cl. ...................................... 514/312; 546/155
(58) Field of Search ........................... 546/155; 514/512

(56) References Cited

FOREIGN PATENT DOCUMENTS

WO  WO 96/04248  *  2/1996

\* cited by examiner

*Primary Examiner*—Zinna Northington Davis
(74) *Attorney, Agent, or Firm*—Larson & Taylor PLC

(57) ABSTRACT

As novel compounds which possess a chymase-inhibiting activity and are useful as medicines for a variety of applications, there are provided SF2809-I substance, SF2809-II substance, SF2809-III substance, SF2809-IV substance, SF2809-V substance and SF2809-VI substance which are represented by the following general formula (VII)

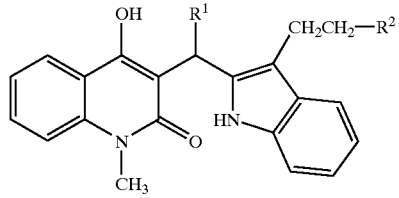

wherein $R^1$ is a hydrogen atom, phenyl group or p-hydroxyphenyl group, and $R^2$ is acetylamino group —$NHCOCH_3$ or hydroxyl group, or pharmaceutically acceptable salts thereof, and which possess the chymase-inhibiting activity. Also provided is a process for the preparation of the above SF2809 substances, as well as a pharmaceutical composition comprising one of those substances.

13 Claims, No Drawings

SF2809-I,II,III,IV,V AND VI SUBSTANCES EXHIBITING CHYMASE-INHIBITING ACTIVITIES

This application is a 371 application of PCT/JP99/06738 filed Dec. 1, 1999.

TECHNICAL FIELD

This invention relates to SF2809-I substance, SF2809-II substance, SF2809-III substance, SF2809-IV substance, SF2809-V substance and SF2809-VI substance or salts thereof, which are novel compounds having a chymase-inhibiting activity. This invention also relates to a process for the preparation of the SF2809-I substance to the SF2809-VI substance. Further, this invention relates to a pharmaceutical composition which contains as an active ingredient SF2809-I, -II, -III, -IV, -V or -VI substance or a pharmaceutically acceptable salt thereof, as well as to a chymase-inhibitor. Furthermore, this invention includes strain SF2809 as a novel microorganism having a characteristic that it is capable of producing the SF2809-I substance to the SF2809-VI substance as above-mentioned.

BACKGROUND ART

An enzyme, chymase, is a chymotripsin-like serine proteinase which is mainly stored in the secretory granules of mast cell and is secreted in tissues of heart, blood vessel, skin and others. As one of the main actions of chymase, there is an action that chymase produces angiotensin II from angiotensin I as substrate.

It has hitherto been thought that the production of angiotensin II is affected basically by the action of angiotensin-converting enzyme (ACE). Recently, however, in the course of study for the elucidation of the production system of angiotensin II in local tissues, it has newly been suggested that there exists a system of production of angiotensin II by a serine proteinase which is different from the angiotensin-converting enzyme. Specifically, it has been clarified that in the left ventricle of human heart, more than 80% of the production of angiotensin II are brought about by serine proteinase [Urata et al., Circ. Res., Vol. 66, pp.883–890 (1990)]. The serine proteinase present in the left ventricle of human heart has been determined for the nucleotide sequence of its encoding gene and thus is identified as a chymase with a molecular weight of about 30,000 [Urata et al, J. Biol. Chem., Vol. 266, pp.17173–17179 (1991)].

It is known in the art that, in the progress of restenosis induced after angiopathy or in cardiomyopathy, there occurs an increase in the chymase activity in the heart. Therefore, a chymase-inhibitor is expected to be useful as a therapeutic agent or a prophylactic agent for hypercardia, cardiac incompetence or arteriosclerosis. It is also known that chymase can promote the degranulation of mast cell, and thus a chymase-inhibitor is also expected to be useful as an anti-inflammatory agent and an antiallergic agent, too.

In addition to the above-mentioned facts, it is also known that chymase has further actions on the production of endothelin and collagenase, and the metabolisms of various physiologically active peptides such as bradykinin, Substance P, neurotensin, somatostatin, VIP, LH-RH, α-MSH and the like, as well as restrictive decomposition of extracellular matrixes such as collagen, fibronectin, vitronectin and the like; decomposition of blood coagulation factors such as thrombin and the like; rise in the secretion reactions of airway mucosa secreting glands; and acceleration in the foam cell-formation of macrophage, and others. Therefore, chymase-inhibitors are also expected to be useful in therapy of asthma, rheumatism, thrombosis or bronchitis, and so on.

PCT Application Publications WO93/25574, WO95/27053 and WO95/27055 disclose some chymase-inhibitors of peptide type among the compounds having the chymase-inhibiting activities. While, chymase-inhibitors of the non-peptide type are disclosed in PCT Application Publication WO96/04248 and European Patent Application First Publication No. 713876. Further, a chymase-inhibitor made of a microbial product is disclosed in Japanese Patent Application Kokai Hei-10-101666.

Hitherto, some compounds having the chymase-inhibiting activity were found. Among of them, however, there was presented no such substance having the chymase-inhibiting activity which has actually been utilized in clinics as a therapeutic drug for treating the above-mentioned diseases. Thus, there is a keen demand to find out such a novel substance which has the chymase-inhibiting activity and which may be useful in clinics.

An object of this invention is to provide a novel compound having an excellent enzyme-inhibiting activity against chymase.

Another object of this invention is to provide a process for the preparation of such a novel compound having a chymase-inhibiting activity. Further objects of this invention are to provide a novel pharmaceutical composition having a chymase-inhibiting activity which is useful as medicine, and also to provide a chymase-inhibitor.

DISCLOSURE OF THE INVENTION

We, the inventors of this invention, have carried out extensive investigations in order to achieve the above-mentioned objects of this invention. As a part of our investigations, we have conducted the screening of microbial metabolites which have a chymase-inhibiting activity. In the course of our research, we cultivated a strain of a family Micromonosporaceae, which is a new microorganism as isolated from a soil sample collected at Hachijo Island, Tokyo, and which is designated as strain SF2809 by us. As a result, we have now found that the resulting culture of strain SF2809 inhibits a human chymase. As a result of further investigations, we have succeeded in isolating and purifying six active compounds having the human chymase-inhibiting activity, from the culture of strain SF2809. We have further found that these six active compounds have such chemical structures as represented by the under-mentioned formulae (I) to (IV), respectively. And, we have confirmed that each of these six active compounds as obtained is a novel compound. Then, we designated these substances as SF2809-I substance, SF2809-II substance, SF2809-III substance, SF2809-IV substance, SF2809-V substance and SF2809-VI substance, respectively. Furthermore, we have confirmed that all and each of the SF2809-I substance of formula (I), SF2809-II substance of formula (II), SF2809-III substance of formula (III), SF2809-IV substance of formula (IV), SF2809-V substance of formula (V) and SF2809-VI substance of formula (VI) as given hereinunder, exhibits an activity inhibitory to a human chymase. Further, these SF2809-I substance to SF2809-VI substance are recognized as a class of compounds which can collectively be represented by the under-mentioned general formula (VII). This invention has been completed on the basis of these findings.

According to a first aspect of this invention, therefore, there is provided a compound which is SF2809-I substance, SF2809-II substance, SF2809-III substance, SF2809-IV substance, SF2809-V substance or SF2809-VI substance each represented by the following general formula (VII)

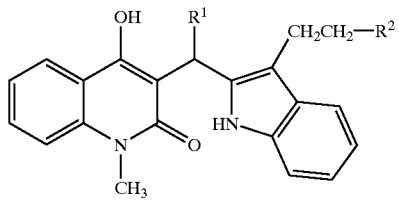
(VII)

wherein $R^1$ is a hydrogen atom, phenyl group or p-hydroxyphenyl group, and $R^2$ is acetylamino group —NHCOCH$_3$ or hydroxyl group; and wherein $R^1$ is hydrogen atom and $R^2$ is acetylamino group for SF2809-I substance; $R^1$ is p-hydroxyphenyl group and $R^2$ is acetylamino group for SF2809-II substance; $R^1$ is hydrogen atom and $R^2$ is hydroxyl group for SF2809-III substance; $R^1$ is p-hydroxyphenyl group and $R^2$ is hydroxyl group for SF2809-IV substance; $R^1$ is phenyl group and $R^2$ is acetylamino group for SF2809-V substance; $R^1$ is phenyl group and $R^2$ is hydroxyl group for SF2809-VI substance, or a pharmaceutically acceptable salt thereof.

As a first example of the compound according to the first aspect of this invention, there is provided SF2809-I substance represented by the following formula (I)

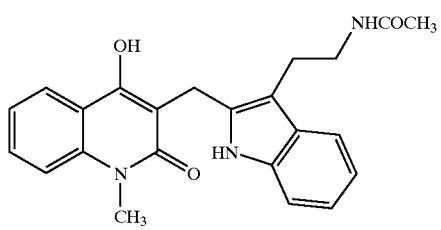
(I)

or a pharmaceutically acceptable salt thereof.

As a second example of the compound according to the first aspect of this invention, there is provided SF2809-II substance represented by the following formula (II)

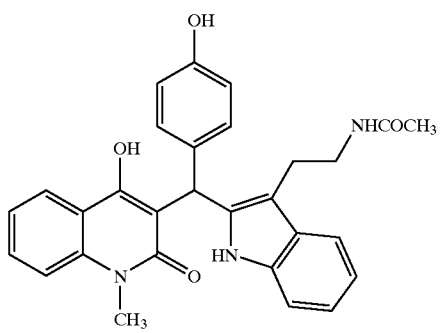
(II)

or a pharmaceutically acceptable salt thereof.

As a third example of the compound according to the first aspect of this invention, there is provided SF2809-II substance represented by the following formula (III)

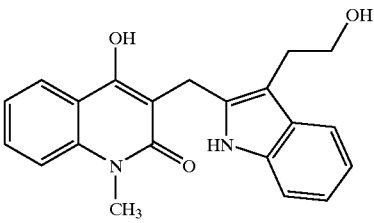
(III)

or a pharmaceutically acceptable salt thereof.

As a fourth example of the compound according to the first aspect of this invention, there is provided SF2809-IV substance represented by the following formula (IV)

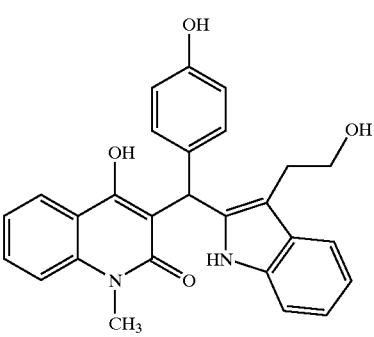
(IV)

or a pharmaceutically acceptable salt thereof.

As a fifth example of the compound according to the first aspect of this invention, there is provided SF2809-V substance represented by the following formula (V)

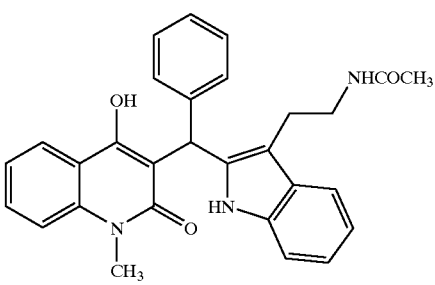
(V)

or a pharmaceutically acceptable salt thereof.

As a sixth example of the compound according to the first aspect of this invention, there is provided SF2809-VI substance represented by the following formula (VI)

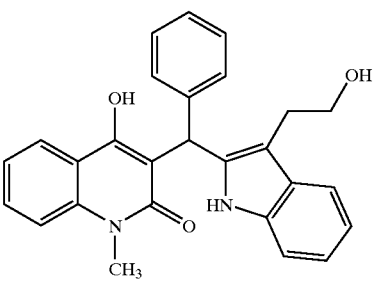
(VI)

or a pharmaceutically acceptable salt thereof.

Pharmaceutically acceptable salts of each of the SF2809-I, SF2809-II, SF2809-III, SF2809-IV, SF2809-V and SF2809-VI substances represented by formulae (I) to (VI) above-mentioned, respectively, include salts with an alkali metal such as sodium, potassium and the like, or salts with an alkaline earth metal such as calcium, barium and the like, as well as acid addition salts with pharmaceutically acceptable inorganic and organic acids.

Summarily, the above-mentioned SF2809-I, SF2809-II, SF2809-III, SF2809-IV, SF2809-V and SF2809-VI substances according to the first aspect of this invention are the compounds which are represented collectively by the following general formula (VII)

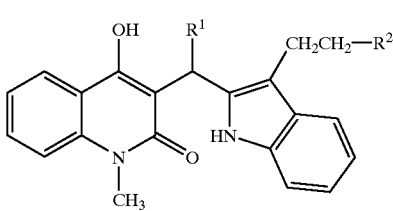

(VII)

wherein $R^1$ is a hydrogen atom, phenyl group or p-hydroxyphenyl group and $R^2$ is acetylamino group —NHCOCH$_3$ or hydroxyl group.

Next, described are physicochemical properties of each of SF2809-I, SF2809-II, SF2809-III, SF2809-IV, F2809-V and SF2809-VI substances according to the first aspect of this invention.

SF2809-I substance according to the first aspect of this invention is represented by formula (I) given above and has the following physicochemical properties.
(1) Color and appearance: Pale yellow colored powder
(2) Molecular formula: $C_{23}H_{23}O_3N_3$
(3) Mass spectrum (FAB-MS): m/z 390 (M+H)$^+$
(4) Ultraviolet absorption spectrum
  When measurement is made in MeOH+1N HCl solution:
    $\lambda_{max}$, nm($\epsilon$): 227 (45900), 277 (10900), 284 (10900), 319 (6420), 332 (5250)
  When measurement is made in MeOH+1N NaOH solution:
    $\lambda_{max}$, nm($\epsilon$) 206 (54900), 222 (54500), 257s (14000), 292 (12100), 310 (11700)
(5) Infrared absorption spectrum (KBr) $\nu_{max}$, cm$^{-1}$: 1630, 1610,1589,1572,1460,1338, 1238,1217,1156,1093,1045, 748
(6) $^1$H-NMR spectrum (CD$_3$OD, 400 MHz)
  $\delta$ (ppm): 1.89 (3H, s), 3.09 (2H, t, J=7.1 Hz), 3.48 (2H, t, J=7.1 Hz), 3.73 (3H, s), 4.17 (2H, s), 6.92 (1H, ddd, J=7.8, 7.1, 1.2 Hz), 6.96 (1H, ddd, J=7.8, 7.1, 1.2 Hz), 7.20 (1H, dd, J=7.8, 1.2 Hz), 7.30 (1H, ddd, J=8.1, 7.1, 1.0 Hz), 7.44 (1H, dd, J=7.8, 1.2 Hz), 7.54 (1H, dd, J=8.5, 1.0 Hz), 7.62 (1H, ddd, J=8.5, 7.1, 1.4 Hz), 8.12 (1H, dd, J=8.1, 1.4 Hz)
(7) $^{13}$C-NMR spectrum (CD$_3$OD, 100 MHz)
  $\delta$ (ppm): 22.1 (t), 22.6 (q), 24.8 (t), 30.2 (q), 41.5 (t), 108.6 (s), 110.1 (s), 111.6 (d), 115.7 (d), 118.5 (d), 118.5 (s), 119.4 (d), 121.5 (d), 122.9 (d), 124.7 (d), 129.7 (s), 131.8 (d), 136.5 (s), 137.1 (s), 140.2 (s), 158.8 (s), 166.2 (s), 173.6 (s)
(8) Solubility: Soluble in methanol, ethyl acetate and dimethylsulfoxide; sparingly soluble in chloroform; and insoluble in hexane and water.

SF2809-II substance according to the first aspect of this invention is represented by formula (II) given above and has the following physicochemical properties.
(1) Color and appearance: Pale red colored powder
(2) Molecular formula: $C_{29}H_{27}O_4N_3$
(3) Mass spectrum (FAB-MS): m/z 482 (M+H)$^+$
(4) Ultraviolet absorption spectrum
  When measurement is made in MeOH+1N HCl solution:
    $\lambda_{max}$, nm($\epsilon$): 227 (68600), 278 (15500), 286 (15500), 322 (10600), 335 (7730)
  When measurement is made in MeOH+1N NaOH solution:
    $\lambda_{max}$, nm($\epsilon$): 207 (93200), 223 (81600), 260s (29000), 283 (23200), 292 (22700), 310s (18800)
(5) Infrared absorption spectrum (KBr)
  $\nu_{max}$, cm$^{-1}$: 1632,1610,1572,1510,1460,1388, 1336,1240, 1172,1089,754
(6) $^1$H-NMR spectrum (CD$_3$OD, 400 MHz)
  $\delta$ (ppm): 1.72 (3H, s), 3.00 (1H, m), 3.14 (1H, m), 3.33 (1H, m), 3.50 (1H, m), 3.70 (3H, s), 6.31 (1H, s), 6.63 (2H, d, J=8.8 Hz), 6.87 (2H, d, J=8.8 Hz), 6.97 (1H, dd, J=7.8, 7.1 Hz), 7.03 (1H, dd, J=8.0, 7.1 Hz), 7.28 (1H, d, J=8.0 Hz), 7.32 (1H, ddd, J=8.1, 7.1, 1.0 Hz), 7.52 (1H, d, J=7.8 Hz), 7.55 (1H, dd, J=8.8, 1.0 Hz), 7.63 (1H, ddd, J=8.8, 7.1, 1.4 Hz), 8.07 (1H, dd, J=8.1, 1.4 Hz)
(7) $^{13}$C-NMR spectrum (CD$_3$OD, 100 MHZ)
  $\delta$ (ppm): 22.5 (q), 25.0 (t), 30.2 (q), 37.7 (d), 41.7 (t), 110.6 (s), 111.9 (d), 114.9 (s), 115.8 (d), 115.9 (d), 115.9 (d), 118.9 (s), 118.9 (d), 119.5 (d), 122.0 (d), 123.1 (d), 124.5 (d), 129.2 (d), 129.2 (d), 129.3 (s), 132.1 (d), 134.6 (s), 136.9 (s), 137.9 (s), 140.2 (s), 156.4 (s), 161.0 (s), 165.7 (s), 173.4 (s)
(8) Solubility: Soluble in methanol, ethyl acetate and dimethylsulfoxide; sparingly soluble in chloroform; and insoluble in hexane and water.

SF2809-III substance according to the first aspect of this invention is represented by formula (III) given above and has the following physicochemical properties.
(1) Color and appearance: Pale yellow colored powder
(2) Molecular formula: $C_{21}H_{20}O_3N_2$
(3) Mass spectrum (FAB-MS): m/z 349 (M+H)$^+$
(4) Ultraviolet absorption spectrum
  When measurement is made in MeOH+1N HCl solution:
    $\lambda_{max}$, nm($\epsilon$): 227 (47000), 276 (10800), 284 (11000), 319 (6450), 332 (5050)
  When measurement is made in MeOH+1N NaOH solution:
    $\lambda_{max}$, nm($\epsilon$): 205 (44300), 223 (46300), 257s (12200), 292 (10500), 310 (10100)
(5) Infrared absorption spectrum (KBr)
  $\nu_{max}$, cm$^{-1}$: 1628,1608,1576,1460,1336,1236, 1155,1093, 1055,1045,758,748
(6) $^1$H-NMR spectrum (CD$_3$OD, 400 MHz)
  $\delta$ (ppm): 3.09 (2H, t, J=6.6 Hz), 3.75 (3H, s), 3.82 (2H, t, J=6.6 Hz), 4.21 (2H, s), 6.92 (1H, ddd, J=7.1, 7.1, 1.2 Hz), 6.96 (1H, ddd, J=7.1, 7.1, 1.4 Hz), 7.18 (1H, dd, J=7.1, 1.2 Hz), 7.28 (1H, ddd, J=8.1, 7.1, 1.2 Hz), 7.41 (1H, dd, J=7.1, 1.4 Hz), 7.55 (1H, dd, J=8.5, 1.2 Hz), 7.63 (1H, ddd, J=8.5, 7.1, 1.2 Hz), 8.05 (1H, dd, J=8.1, 1.2 Hz)
(7) $^{13}$C-NMR spectrum (CD$_3$OD, 100 MHz)
  $\delta$ (ppm): 22.2 (t), 28.3 (t), 30.3 (q), 63.8 (t), 108.8 (s), 110.0 (s), 111.5 (d), 115.6 (d), 118.2 (s), 118.4 (d), 119.4 (d), 121.5 (d), 123.1 (d), 124.4 (d), 129.6 (s), 132.0 (d), 135.6 (s), 137.1 (s), 140.0 (s), 159.7 (s), 166.2 (s)
(8) Solubility: Soluble in methanol, ethyl acetate and dimethylsulfoxide; sparingly soluble in chloroform; and insoluble in hexane and water.

SF2809-IV substance according to the first aspect f this invention is represented by formula (IV) given above and has the following physicochemical properties.
(1) Color and appearance: Pale red colored powder
(2) Molecular formula: $C_{27}H_{24}O_4N_2$
(3) Mass spectrum (FAB-MS): m/z 441 $(M+H)^+$
(4) Ultraviolet absorption spectrum
  When measurement is made in MeOH+1N HCl solution:
    $\lambda_{max}$, nm($\epsilon$): 228 (57400), 280 (14500), 323 (8020), 334 (6170)
  When measurement is made in MeOH+1N NaOH solution:
    $\lambda_{max}$, nm($\epsilon$): 205 (75700), 223 (58000), 260s (16700), 286 (16000), 293 (16000), 310 (13600)
(5) Infrared absorption spectrum (KBr)
    $\nu_{max}$, cm$^{-1}$: 1630,1610,1574,1510,1460,1388, 1338,1240, 1091,1045,756
(6) $^1$H-NMR spectrum (CD$_3$OD, 400 MHz)
    δ (ppm): 3.05 (1H, m), 3.13 (1H, m), 3.71 (3H, s), 3.73 (2H, m), 6.27 (1H, s), 6.63 (2H, d, J=8.8 Hz), 6.83 (2H, d, J=8.8 Hz), 6.98 (1H, dd, J=7.8, 7.1 Hz), 7.04 (1H, dd, J=7.8, 7.1 Hz), 7.29 (1H, d, J=7.8 Hz), 7.33 (1H, ddd, J=8.1, 7.1, 1.0 Hz), 7.52 (1H, d, J=7.8 Hz), 7.57 (1H, dd, J=8.5, 1.0 Hz), 7.65 (1H, ddd, J=8.5, 7.1, 1.4 Hz), 8.08 (1H, dd, J=8.1, 1.4 Hz)
(7) $^{13}$C-NMR spectrum (CD$_3$OD, 100 MHz)
    δ (ppm): 28.7 (t), 30.3 (q), 38.1 (d), 63.8 (t), 110.2 (s), 111.9 (d), 115.1 (s), 115.8 (d), 115.9 (d), 115.9 (d), 118.1 (s), 118.9 (d), 119.6 (d), 122.1 (d), 123.3 (d), 124.5 (d), 129.1 (d), 129.1 (d), 129.4 (s), 132.2 (d), 134.3 (s), 136.9 (s), 137.7 (s), 140.2 (s), 156.5 (s), 159.9 (s), 165.6 (s)
(8) Solubility: Soluble in methanol, ethyl acetate and dimethylsulfoxide; sparingly soluble in chloroform; and insoluble in hexane and water.

SF2809-V substance according to the first aspect of this invention is represented by formula (V) given above and has the following physicochemical properties.
(1) Color and appearance: Colorless powder
(2) Molecular formula: $C_{29}H_{27}O_3N_3$
(3) Mass spectrum (FAB-MS): m/z 466 $(M+H)^+$
(4) Ultraviolet absorption spectrum
  When measurement is made in MeOH+1N HCl solution:
    $\lambda_{max}$, nm($\epsilon$): 227 (62800), 278 (14400), 284 (14000), 323 (9120), 335 (6980)
  When measurement is made in MeOH+1N NaOH solution:
    $\lambda_{max}$, nm($\epsilon$): 207 (83700), 222 (75300), 257s (23700), 284 (17700), 292 (18100), 310 (15800)
(5) Infrared absorption spectrum (KBr)
    $\nu_{max}$, cm$^{-1}$: 1632,1611,1589,1572,1460,1387,1338, 1244, 1213,1157,1089,754
(6) $^1$H-NMR spectrum (CD$_3$OD, 400 MHz)
    δ (ppm): 1.68 (3H, s), 3.04 (1H, m), 3.18 (1H, m), 3.33 (1H, m), 3.55 (1H, m), 3.67 (3H, s), 6.42 (1H, s), 6.95 (1H, dd, J=7.6, 7.1 Hz), 7.01 (1H, dd, J=8.1, 7.1 Hz), 7.02 (2H, m), 7.06 (1H, m), 7.14 (2H, m), 7.23 (1H, ddd, J=8.1, 7.1, 1.0), 7.27 (1H, d, J=8.1 Hz), 7.47 (1H, dd, J=8.5, 1.0 Hz), 7.52 (1H, d, J=7.6 Hz), 7.56 (1H, ddd, J=8.5, 7.1, 1.2 Hz), 8.11 (1H, dd, J=8.1, 1.2 Hz)
(7) $^{13}$C-NMR spectrum (CD$_3$OD, 100 MHz)
    δ (ppm): 22.4 (q), 24.9 (t), 30.1 (q), 38.2 (d), 41.7 (t), 110.2 (s), 111.8 (d), 113.5 (s), 115.5 (d), 118.9 (d), 119.4 (d), 120.8 (s), 121.9 (d), 122.6 (d), 125.1 (d), 126.3 (d), 128.0 (d), 128.0 (d), 128.9 (d), 128.9 (d), 129.2 (s), 131.6 (d), 136.9 (s), 138.7 (s), 140.5 (s), 144.9 (s), 165.3 (s), 166.1 (s), 173.4 (s)
(8) Solubility: Soluble in methanol, ethyl acetate, dimethylsulfoxide and chloroform; and insoluble in hexane and water.

SF2809-VI substance according to the first aspect of this invention is represented by formula (VI) given above and has the following physicochemical properties.
(1) Color and appearance: Colorless powder
(2) Molecular formula: $C_{27}H_{24}O_3N_2$
(3) Mass spectrum (FAB-MS): m/z 425 $(M+H)^+$
(4) Ultraviolet absorption spectrum
  When measurement is made in MeOH+1N HCl solution:
    $\lambda_{max}$, nm($\epsilon$): 227 (50200), 278 (11900), 322 (7490), 334 (5960)
  When measurement is made in MeOH+1N NaOH solution:
    $\lambda_{max}$, nm($\epsilon$): 205 (51700), 223 (51100), 258s (13200), 293 (10500), 310 (9790)
(5) Infrared absorption spectrum (KBr)
    $\nu_{max}$, cm$^{-1}$: 1624,1610,1589,1574,1460,1395, 1386,1338, 1214,1157,1091,1043,756
(6) $^1$H-NMR spectrum (CD$_3$OD, 400 MHz)
    δ (ppm): 3.08 (1H, m), 3.18 (1H, m), 3.68 (3H, s), 3.73 (2H, m), 6.41 (1H, s), 6.96 (1H, ddd, J=7.8, 7.1, 1.2 Hz), 7.00 (2H, m), 7.01 (1H, ddd, J=7.8, 7.1, 1.2 Hz), 7.06 (1H, m), 7.14 (2H, m), 7.25 (1H, ddd, J=8.1, 7.1, 1.0 Hz), 7.27 (1H, dd, J=7.8, 1.2 Hz), 7.49 (1H, dd, J=8.5, 1.0 Hz), 7.51 (1H, dd, J=7.8, 1.2 Hz), 7.57 (1H, ddd, J=8.5, 7.1, 1.4 Hz), 8.12 (1H, dd, J=8.1, 1.4 Hz)
(7) $^{13}$C-NMR spectrum (CD$_3$OD, 100 MHz)
    δ (ppm): 28.8 (t), 30.1 (q), 38.4 (d), 63.9 (t), 109.6 (s), 111.7 (d), 113.4 (s), 115.4 (d), 118.8 (d), 119.3 (d), 120.9 (s), 121.7 (d), 122.6 (d), 125.3 (d), 126.3 (d), 128.0 (d), 128.0 (d), 128.8 (d), 128.8 (d), 129.4 (s), 131.6 (d), 136.8 (s), 138.8 (s), 140.5 (s), 144.9 (s), 165.4 (s), 166.2 (s)
(8) Solubility: Soluble in methanol, ethyl acetate, dimethylsulfoxide and chloroform; and insoluble in hexane and water.

Further, in a second aspect of this invention, there is provided a process for the production of the SF2809-I substance, SF2809-II substance, SF2809-III substance, SF2809-IV substance, SF2809-V substance and/or SF2809-VI substance as defined hereinbefore, characterized in that the process comprises cultivating a microbial strain which belongs to the genus Dactylosporangium and which produces at least one of SF2809-I substance of formula (I) above, SF2809-II substance of formula (II) above, SF2809-III substance of formula (III) above, SF2809-IV substance of formula (IV) above, SF2809-V substance of formula (V) above and SF2809-VI substance of formula (VI) above, and then recovering from the resulting culture at least one of the SF2809-I substance, SF2809-II substance, SF2809-III substance, SF2809-IV substance, SF2809-V substance and SF2809-VI substance.

The microbial strain, which is to be used in the process of the second aspect of this invention for the production of at least one of SF2809-I, -II, -III, -IV, -V and -VI substances, is sometime hereinafter abbreviated simply as "SF2809 substance-producing strain".

As such SF2809 substance-producing strain mentioned above, there may be exemplified the strain SF2809 which was newly isolated from a soil sample collected by us at Hachijo Island, Tokyo, and which is recognized to belong to the family Micromonosporaceae. The microbiological properties of the strain SF2809 are mentioned below.

By the way, it may be added that the SF2809 substance-producing strain to be used in the process of this invention is not to be limited to such specific microbial strain as described in this specification. There may be used any of the SF2809 substance-producing strains, so far as it has an ability to produce at least one of the SF2809-I substance to SF2809-VI substance. As preferred examples of the microorganisms which may be used for this purpose, there may be mentioned the strain SF2809, or subcultures of strain SF2809, as well as artificial variants and natural variants thereof.

Properties of the strain SF2809 mentioned above are now given.

1. Microbiological Properties of Strain SF2809

Culture media and methods used for studying the morphological observations, cultural characteristics and physiological properties of strain SF2809 were mainly in accordance with those indicated by Shirling, E. B. and Gottlieb, D., (Int. J. Syst. Bacteriol., Vol. 16, pp. 313–340, 1966) and by Waksman, S. A., (The actinomycetes, Vol. 2: Classification, Identification and Description of genera and species. The Williams and Wilkins Co., Baltimore, 1961). In making the morphological observations, this strain SF2809 was cultivated in ISP media, yeast extract-starch-agar medium (comprising yeast extract 0.2%, starch 1.0%, agar 18 g, purified water 1 L, pH 7.0), calcium malate-agar medium or sodium malate-agar medium or sodium succinate-agar medium (Shomura, T., Actinomycetol, Vol. 7, pp.88–98, 1993), and the necessary observation was made under an optical microscope and a scanning electron microscope. In main cases, the strain SF2809 was cultivated at 28° C. for 14 days. Color identification was made in accordance with Color Harmony Manual (Container Corporation of America, 1958.). Further, the amino acid analysis of the cell wall of strain SF2809 was made in accordance with Becker et al's method (Becker et al, Appl. Microbiol., Vol. 12, pp.421–423, 1964), and the sugar composition of the whole cell of strain SF2809 was analyzed in accordance with Lechevalier et al's method (Int. J. Syst. Bacteriol., Vol. 20, pp.435–443, 1970), and the acyl type of peptidoglycan in the cell wall was analyzed in accordance with Uchida et al's method (J. Gen. Appl. Microbiol, Vol. 23, pp.249–260, 1977). Further, phylogenetic analysis of 16SrRNA sequence of the strain SF2809 was investigated.

(1) Morphological Characteristics

The vegetative mycelia of strain SF2809 have a diameter of 0.4–0.5 μm and develop well with irregular branches, but without fragmentation. Aerial mycelium is not observed. Many spore-like structures, which are each in a sphere form, are formed in the vegetative mycelia, and their diameter is 1.0–1.6 μm and their surface is smooth or slightly rough. There are not observed such sporangia which are in the form of finger or rod extending from the vegetativ emycelia into the air.

(2) Cultural Characteristics and Physiological Properties

The cultural characteristics and physiological properties of strain SF2809 are shown in Table 1 and Table 2, and the utilization of carbon sources by this strain is shown in Table 3 below. The growth of the strain SF2809 is ordinary or poor in many media, and in all the media used the spherical spore-like structures were observed. The color of vegetative mycelia is orange or orange-brown. Such discoloration of colonies into black and humectation of colonies during the aging which are usually observed for typical strains of the family Micromonosporaceae, are not observed for the strain SF2809.

TABLE 1

Culture characteristics of strain SF2809

| Medium | Growth | Color of vegetative mycelia | Soluble pigment | Aerial hyphae |
|---|---|---|---|---|
| Yeast-malt-agar (ISP medium No.2) | average | apricot (4 ga) | none | none |
| Oatmeal-agar (ISP medium No.3) | abundant | russet orange (4 nc) | none | none |
| Inorganic salt-starch-agar (ISP medium No.4) | abundant | dark luggage tan (4 pg) | none | none |
| Glycerol-asparagine-agar (ISP medium No.5) | poor | light melon yellow (3 ea) | none | none |
| Peptone-yeast-iron-agar (ISP medium No.6) | poor | bright melon yellow (3 ia) | none | none |
| Tyrosine-agar (ISP medium No.7) | poor | light melon yellow (3 ea) | none | none |
| Yeast-starch-agar | abundant | orange rust (4 pe) | none | none |
| Bennett-agar | abundant | cinnamon yellow maple (3 le) | none | none |
| Calcium malate-agar | poor | melon yellow (3 ga) | none | none |
| Sodium malate-agar | poor | light melon yellow (3 ea) | none | none |
| Sodium succinate-agar | poor | light melon yellow (3 ea) | none | none |

TABLE 2

Physiological properties of strain SF2809

| Conditions | Properties |
|---|---|
| Temperature range for growth (Optimum) | 15–37° C. (28° C.) |
| Liquefaction of gelatin | – ~ (+) |
| Coagulation of milk | – ~ (+) |
| Peptonization of milk | – ~ (+) |
| Hydrolysis of starch | + |
| Reduction of nitrate | + |
| Production of melanoid pigment | – |
| Sodium chloride tolerance | ≦1% |

TABLE 3

Utilization of carbon sources of strain SF2809

| Carbon sources | Growing |
|---|---|
| D-glucose | + |
| Sucrose | + |
| D-xylose | + |
| D-fructose | + |
| L-rhamnose | + |
| Raffinose | + |
| L-arabinose | +– |
| Inositol | – |
| Mannitole | + |

Note:
+: Utilizable; +–: Weakly utilizable; –: Not utilizable; Basal medium: ISP medium No.9

(3) Chemotaxonomical Properties

In view of the fact that the presence of meso-diaminopimelic acid and glycine in the cell wall of strain SF2809 is confirmed; and that arabinose and xylose were detected in the hydrolysate of the whole cell of strain SF2809, it is concluded that the strain SF2809 is classified into the IID type of the cell wall chemotype according to Lechevalier et al' classification. The acyl type of peptidoglycan is of a glycolate type but no mycolic acid is detected. Main menaquinones are composed of MK-9($H_6$) and MK-9 ($H_8$) which are present in substantially the same proportions and totally amount to 90% of the menaquinones. Cellular fatty acids of strain SF2809 are composed mainly of about 80% of branched fatty acids, including iso-C16:0, iso-C15:0, anteiso-C17:0, anteiso-C15:0 and iso-C17:0 fatty acids; and are composed of 5–10% each of mono-unsaturated branched fatty acids and straight saturated fatty acids as minor components. 10-Methyl fatty acid and hydroxyfatty acid are not observed.

In view of the above morphological and chemotaxonomical properties, it is strongly suggested that the strain SF2809 belongs to the family Micromonosporaceae.

(4) Genetic Analysis

An almost complete 16SrRNA sequence of strain SF2809 has been analyzed (Accession number: AB017374) and compared with that of some representative strains in the order Actinomycetales. From these comparisons, the strain SF2809 can be classified in a cluster of the genus Dactylosporangium.

From such chemotaxonomical properties and genetic analysis as above-mentioned, there is suggested a great possibility that strain SF2809 would belong to the genus Dactylosporangium. On examining actually strain SF2809 as grown on the different culture media, however, it could not be observed that there occurs the formation of such finger-like sporangia which is characteristic to the genus Dactylosporangium. Thus, it cannot be yet concluded perfectly that strain SF2809 belongs to the genus Dactylosporangium according to the current system of classification of the order Actinomycetales. It is still allowable to recognize that strain SF2809 is one strain of actinomycetes which is belonging to the family Micromonosporaceae. On the other hand, strain SF2809 produces the spherical structures abundantly formed, and such spherical structures produced by strain SF2809 closely resemble to the spherical structures which are called globose body that are often formed by the known strains of the genus Dactylosporangium. Further, Ensign et al have announced that globose body can germinate and thus is a sort of spores (Ensign, J. C., Ann. Rev. Microbiol., Vol. 32, pp.185–219, 1978).

Taking the above-mentioned observations and the paior art teachings together into consideration, it is tentatively judged that strain SF2809 is one strain which is belonging to the genus Dactylosporangium with having lost the capability of producing sporangium. We are still continuing our investigation as to whether we can decide strain SF2809 to be one of the strains belonging to the genus Dactylosporangium.

Strain SF2809 has been deposited in the Japanese depository "National Institute of Bioscience and Human-Technology, Agency of Industrial Science and Technology" which locates at Tsukuba-City, Ibaraki Prefecture, Japan, since August 31, 1998 under the deposit number FERMP-16975. Then since Sep. 16, 1999, the strain SF2809 has been deposited in the same Institute under the deposit number of FERM BP-6872 in terms of the Budapest Treaty.

Now, particular procedures for the preparation of at least one of SF2809-I substance to SF2809-IV substance by the process according to the second aspect of this invention are illustrated.

(1) Cultivation of an SF2809 Substance-producing Strain

In the process according to the second aspect of this invention, an SF2809 substance-producing strain, preferably, for example, the aforesaid strain SF2809 is cultivated in a nutrient medium containing suitable carbon sources and nitrogen sources. The culture medium to be used may be either a natural medium or a synthetic medium. As the carbon sources, there may be used carbohydrates such as glucose, fructose, sucrose, molasses, starch or starch hydrolysates, etc., and organic acids such as acetic acid, propionic acid, etc. or alcohols such as glycerine, etc. As the nitrogen sources, on the other hand, there are usually used peptone, meat extract, yeast extract, corn steep liquor, oatmeal, wheat germ, casein hydrolysate, soybean meal and soybean meal hydrolysate, etc., but it is also effective to use inorganic and organic nitrogen compounds such as ammonium salts (for example, ammonium chloride, ammonium sulfate, ammonium nitrate, ammonium phosphate, etc.), urea, amino acids, etc. These carbon sources and nitrogen sources may be used in combination with each other.

If necessary, to the culture medium used, there may be added potassium dihydrogen phosphate, potassium hydrogen phosphate, magnesium phosphate, magnesium sulfate, sodium chloride, ferrous sulfate, manganese sulfate, copper sulfate, calcium carbonate or other inorganic salts. In cases where the culture medium is foamed, there may be added liquid paraffin, animal oils, vegetable oils, mineral oils or silicone oils, etc.

The cultivation of the SF2809 substance-producing strain may be carried out under aerobic conditions by a shaking cultivation method or a submerged cultivation method under aeration and stirring, and so on. The available cultivation temperature may vary appropriately within the range of temperature where the SF2809 substance-producing strain used is able to produce the target substances intended, but a temperature of 15~37° C. is preferred. The cultivation period of time is usually 1~10 days. After the completion of the cultivation, at least one of the target SF2809 substances is recovered from the resulting culture, and then it is purified.

(2) Recovery and Purification of SF2809 Substances

Upon recovering the SF2809 substance(s) of this invention from the resulting culture of the microorganism, the resulting culture is first separated into the mycelia and the culture broth filtrate, by filtration or centrifugation. Then, the SF2809 substance(s) may be separated, isolated and purified by conventional separating methods, which may be such separation methods as solvent extraction, adsorption-desorption with use of an adsorber, chromatographic separation with use of a variety of resins, precipitation and others, in any suitable combination. For instance, SF2809 substance(s) may be extracted from the mycelia of strain SF2809 by adding acetone to the culture of strain SF2809, followed by filtration of the resulting mixture. Then, the acetone is distilled off from the resultant filtrate (the acetone extract) and the resulting aqueous solution is extracted with ethyl acetate. The ethyl acetate extract so obtained is then subjected to chromatographic separation and purification with using column of silica gel, column of Sephadex LH-20 and column of ODS, in order. Finally, fractionating operations by HPLC or TLC may be effected to isolate the SF2809-I substance to SF2809-VI substance from each other.

As mentioned above, each of the SF2809-I substance to SF2809-VI substance according to the first aspect of this invention possesses an activity inhibitory to chymase. The chymase-inhibiting activity of SF2809 substances are examined by the following Test Example.

TEST EXAMPLE 1

In this Example, the chymase-inhibiting activity of SF2809 substances was determined as described below.

(1) Preparation of the Enzyme, Chymase

A human recombinant chymase was prepared in accordance with the method of Urata et al's report (Urata et al., J. Biol. Chem., Vol. 266, p.17173, 1991). Thus, cultivation was made of insect cells (Tn5) which had been infected with recombinant baculovirus containing therein such cDNA that encodes the human chymase. The resulting culture of the insect cells was filtered and the resultant supernatant was treated with Heparin-sepharose (Pharmacia's product) to recover the chymase. The chymase so recovered was then purified. Then, the purified chymase was activated in accordance with the method of Murakami et al's report (Murakami et al, J. Biol. Chem., Vol. 270, p.2218, 1991), after which the activated chymase was purified with Heparin-sepharose to afford an activated type of human chymase.

(2) Determination of Chymase-inhibiting Activity

To 50 μl of a buffer A (comprising 0.5~3.0 M NaCl, 50 mM tris hydrochloric acid, pH 8.0) which contained 1~5 ng of the active-type of human chymase as prepared in (1) above, there was added 2 μl of a solution in dimethylsulfoxide (DMSO) of an SF2809 substance as the test substance. Then, to the resulting mixture, there was added 50 μl of a buffer A which contained 0.5 mM of succinyl-alanyl-histidyl-prolyl-phenylalanyl-para-nitroanilide (Buckem's product) as a substrate. The resultant admixture was incubated at room temperature for 5 minutes. The change in the absorbance at 405 nm of the reaction solution was measured with passage of the incubation time, thereby to examine the chymase-inhibiting activity of the SF2809 substance under test.

(3) Test Result

It is found that the SF2809-I substance to SF2809-VI substance according to this invention showed a high activity inhibitory to chymase such that their 50% inhibitory concentrations ($IC_{50}$) against the human chymase are in the range of $7.3 \times 10^{-6}$ M~$1.4 \times 10^{-8}$ M.

To be concrete, it is found that the $IC_{50}$ values of SF2809-I substance, -II substance, -III substance, -IV substance, -V substance and -VI substance are $7.3 \times 10^{-6}$ M, $4.1 \times 10^{-8}$ M, $2.1 \times 10^{-6}$ M, $8.1 \times 10^{-8}$ M, $4.3 \times 10^{-8}$ M and $1.4 \times 10^{-8}$ M, respectively.

As is clear from the Test Example above, all and each of the SF2809-I, SF2809-II, SF2809-III, SF2809-IV, SF2809-V and SF2809-VI substances exhibit a chymase-inhibiting activity. Therefore, each of the SF2809-I substance to SF2809-VI substance is utilizable for their chymase-inhibiting activity and is useful for the therapeutic treatment or the prevention of cardiac infarction, cardiomegaly, cardiac insufficiency, myocardosis, arteriosclerosis, hypertension, hemangioendotyrosis, peripheral cardiovascular disorder, renal insufficiency, allergy, various inflammations, atopic dermatitis, rheumatism, asthma and bronchitis, for example. Each of the SF2809 substances according to this invention may be formulated in admixture with any conventional and pharmaceutically acceptable solid or liquid carrier(s) to prepare a pharmaceutical composition.

According to a third aspect of this invention, therefore, there is provided a pharmaceutical composition which comprises as an active ingredient SF2809-I substance, SF2809-II substance, SF2809-III substance, SF2809-IV substance, SF2809-V substance or SF2809-VI substance as above-defined, or a pharmaceutically acceptable salt thereof, in combination with a pharmaceutically acceptable carrier.

The pharmaceutical composition according to the third aspect of this invention possesses a chymase-inhibiting activity and may be administered as a medicine to animals, including human beings. To be concrete, the composition according to the third aspect of this invention is effective for the therapy or prevention of cardiac infarction, cardiomegaly, cardiac insufficiency, myocardosis, arteriosclerosis, hypertension, hemangioendotyrosis, peripheral cardiovascular disorder, renal insufficiency, allergy, various inflammations, atopic dermatitis, rheumatism, asthma, bronchitis, and others.

In the pharmaceutical composition according to the third aspect of this invention, the carrier to be incorporated may be a solid or liquid carrier which is conventionally used in the pharmaceutical art. The solid carrier may, for example, be starch, lactose, crystalline cellulose or calcium carbonate, and the liquid carrier may, for example, be physiological saline, aqueous ethanol or ethanol. The proportion of SF2809 substance as an active ingredient in the composition is not specifically limited, so far as it is sufficient to treat therapeutically the disease as intended, but it is usually in the range of 0.01%~100%, preferably 0.1%~80%, on the basis of the total weight of the composition.

The pharmaceutical composition according to the third aspect of this invention, when administered, may be formulated into a preparation in a usual manner, depending upon the nature of various carrier used, the manner of administration or the direction of use of the drug.

As the preparation for oral administration, there may be exemplified tablets, pills, granules, capsules, powder, liquid, syrup, sublingual tablets, etc. On the other hand, as the preparation for parenteral administration, there may be exemplified injections, percutaneouly absorbable agents, inhalations, suppository, and the like. Upon formulating the composition of this invention, there may be used, if desired, a variety of additives for pharmaceutical purposes, such as surface active agent, excipient, stabilizer, wetting agent, collapsing agent, solubilizing aid, isotonic agent, buffering agent, coloring agent, perfuming agent, etc.

Dosage of SF2809-I substance to SF2809-VI substance as medicine to be administered may vary depending upon the age and body weight of patient, the nature and extent of disease and the route of administration. Usually, the SF2809 substance may be administered at a dosage in the range of 0.01~1000 mg/kg/day for oral administration to adult human beings and in the range of 0.001~100 mg/kg/day for intravenous administration.

According to a fourth aspect of this invention, further, there is provided a chymase inhibitor consisting of SF2809-I substance of formula (I), SF2809-II substance of formula (II), SF2809-III substance of formula (III), SF2809-IV substance of formula (IV), SF2809-V substance of formula (V) or SF2809-VI substance of formula (VI) as above-mentioned or a pharmaceutically acceptable salt thereof. For the chymase inhibitor according to the fourth aspect of this invention, each of SF2809-I substance to SF2809-VI substance or a salt thereof may be used by itself, for example, as a reagent to test the enzyme.

Furthermore, according to a fifth aspect of this invention, there is provided as a new microorganism, strain SF2809, which belongs to the genus Dactylosporangium and which has the above-mentioned microbiological properties, which is characterized by its capability of producing SF2809-I substance of formula (I), SF2809-II substance of formula (II), SF2809-III substance of formula (III), SF2809-IV substance of formula (IV), SF2809-V substance of formula (V) and SF2809-VI substance of formula (VI) as given hereinbefore, and which has been deposited under a deposit number of FERM BP-6872 in National Institute of Bioscience and Human-Technology, Agency of Industrial Science and Technology.

BEST MODE FOR CARRYING OUT THE INVENTION

This invention is now illustrated by the following Examples. However, this invention is in no way limited thereto, but includes all of variations and modifications which are not disclosed herein.

EXAMPLE 1

Production of SF2809 Substance (1) Cultivation of an SF2809 Substance-producing Strain Into three 100 ml-Erlenmeyer flasks were poured 20 ml portions of a pre-incubation medium comprising 1.0% glucose, 2.0% soluble starch, 0.3% yeast extract, 0.5% polypeptone, 0.6% wheat germ, 0.2% soybean meal and 0.2% calcium carbonate and which had been adjusted a pH of 7.0 with 6N NaOH. The pre-incubation medium was sterilized at 120° C. for 20 minutes. Each portion of the medium so sterilized in the flasks was then inoculated with one loopful amount of strain SF2809 (deposited under FERM BP-6872) which had been incubated on an agar plate. The pre-incubation medium so inoculated was subsequently shake-cultivated at 28° C. for 4 days. Another 200 ml-portions of the pre-cultivation medium of the same composition as above were poured into each of fresh three 2 L Erlenmeyer flasks, and the medium placed in each flask was sterilized at 120° C. for 20 minutes. To the pre-incubation medium so sterilized in each of the latter flasks was then transplanted the total volume of the culture broth which was obtained from the shake-cultivation in the first-mentioned flasks. The resulting mixture was shake-cultivated at 28° C. for 2 days to obtain a seed culture broth.

On the other hand, into four 50 liter-jar fermentors were poured 30 liters-portions of a productive culture medium comprising 2.0% glucose, 1.0% soluble starch, 1.5% soybean meal, 0.1% polypeptone, 0.8% wheat germ, 0.1% "Staminol", 0.1% sodium chloride and 0.2% calcium carbonate and which had been adjusted a pH of 8.0 with 6N NaOH. The culture medium in each fermentor was sterilized at 120° C. for 20 minutes. Then, under sterile conditions, the culture medium was inoculated with the total amount of the seed culture broth as obtained hereinbefore. The cultivation was made at 28° C. for 5 days, while the stirring was effected at 250 rpm and the aeration was at 17.5 L/min.

(2) Recovery and Purification of SF2809 Substances

The culture broth (120 L) obtained as above was centrifuged so that it was separated into the mycelia and the supernatant. The supernatant was then extracted with ethyl acetate (100 L) under stirring. The mycelia were extracted with 50% aqueous acetone (50 L), and the resulting acetone extract as separated from the mycelia was distilled under a reduced pressure to remove the acetone therefrom. The resultant aqueous solution was extracted with ethyl acetate (30 L). The extracts in ethyl acetate so obtained were combined together and concentrated under a reduced pressure to obtain a crude extract (56 g) containing the SF2809 substances. This crude extract was washed with hexane (2 L) and then dissolved in methanol (500 ml). To the resulting methanolic solution was added 150 g of a silica gel (Wakogel C300, a product of Wako Pure Chemical Co.), and the resulting mixture was subjected to evaporation to dryness under a reduced pressure.

The resultant powder containing the silica gel was subsequently placed onto a silica gel layer (300 g) positioned on a glass filter. The powder of silica gel containing the crude extract adsorbed was then washed with chloroform (3 L) and then eluted with 3% methanol-chloroform (4 L). The eluate so obtained was concentrated to dryness under a reduced pressure to give 20 g of a dried solid. This solid was dissolved in a small volume of methanol. The resulting solution was applied, in three portions and successively, to a column of Sephadex LH-20 (2000 ml, a product of Pharmacia). The column was eluted with methanol to collect active fractions of the eluate. All the active fractions were collected together and evaporated to dryness to give a residue(1.9 g).

The resulting dried residue was dissolved in a small volume of methanol, to which was then added 2-fold volume of water. The methanolic solution thus obtained was put on the top of a column of "Cosmosil" (300 ml, a product of Nacalai tesque) which had been packed with aid of 30% acetonitrile-water. The Cosmosil column was eluted firstly with 30% aqueous acetonitrile and then with 70% aqueous acetonitrile, and the active fractions so eluted were collected together and evaporated to dryness to give a residue (107 mg). The resulting residue of the active fractions was dissolved in a small volume of methanol. The resulting methanolic solution was poured, in three portions and successively, into a column of Inertsil ODS-2 (inner diameter 2 cm×25 cm, a product of GL Science) for high-performance liquid chromatography (HPLC). This column was then eluted in a gradient manner with 40%~65% acetonitrile-water. By this elution, six fractions were successively obtained as the active fractions. Each of these six active fractions was independently evaporated to dryness. Thus, there were separately yielded SF2809-I substance (2.3 mg), SF2809-II substance (1.3 mg), SF2809-III substance (2.3 mg), SF2809-IV substance (2.7 mg), SF2809-V substance (1.1 mg) and SF2809-VI substance (1.0 mg).

INDUSTRIAL APPLICABILITY

As explained hereinbefore, according to this invention, there are provided SF2809-I substance, SF2809-II substance, SF2809-III substance, SF2809-IV substance, SF2809-V substance and SF2809-VI substance, or a pharmaceutically acceptable salt thereof, which all have a chymase-inhibiting activity. Also provided is a process for the preparation of SF2809-I to SF2809-VI substances. It is expected that the SF2809-I to SF2809-I substances according to this invention are useful and effective for a therapeutic treatment and prevention of various disorders in which chymase can participate.

What is claimed is:

1. A compound, which is SF2809-I substance, SF2809-II substance, SF2809-III substance, SF2809-IV substance, SF2809-V substance or SF2809-VI substance each represented by the following formula (VII)

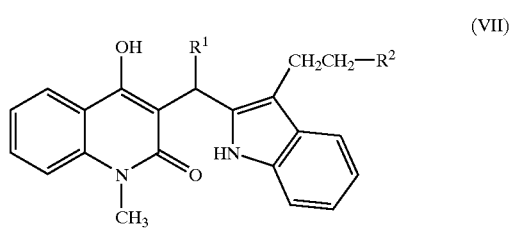

wherein $R^1$ is a hydrogen atom, phenyl group or p-hydroxyphenyl group, and $R^2$ is acetylamino group —NHCOCH$_3$ or hydroxyl group, and wherein R$^1$ is hydrogen atom and R$^2$ is acetylamino group for SF2809-I substance; R$^1$ is p-hydroxyphenyl group and R$^2$ is acetylamino group for SF2809-II substance; R$^1$ is hydrogen atom and R$^2$ is hydroxyl group for SF2809-III substance; R$^1$ is p-hydroxyphenyl group and R$^2$ is hydroxyl group for SF2809-IV substance; R$^1$ is phenyl group and R$^2$ is acetylamino group for SF2809-V substance; and R$^1$ is phenyl group and R$^2$ is hydroxyl group for SF2809-VI substance, or a pharmaceutically acceptable salt thereof.

2. A compound according to claim 1, which is SF2809-I substance represented by the following formula (I)

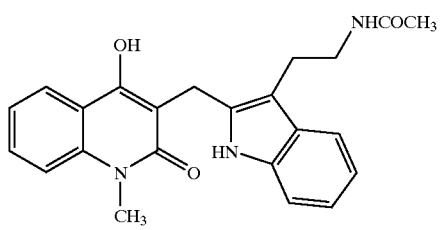

(I)

or a pharmaceutically acceptable salt thereof.

3. A compound according to claim 1, which is SF2809-II substance represented by the following formula (II)

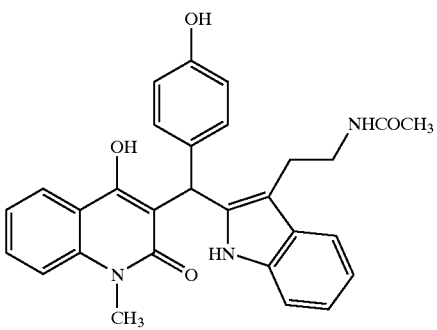

(II)

or a pharmaceutically acceptable salt thereof.

4. A compound according to claim 1, which is SF2809-III substance represented by the following formula (III)

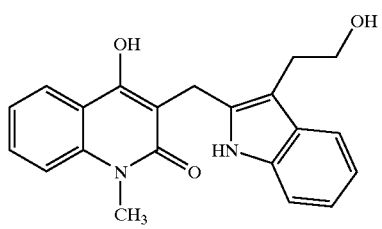

(III)

or a pharmaceutically acceptable salt thereof.

5. A compound according to claim 1, which is SF2809-IV substance represented by the following formula (IV)

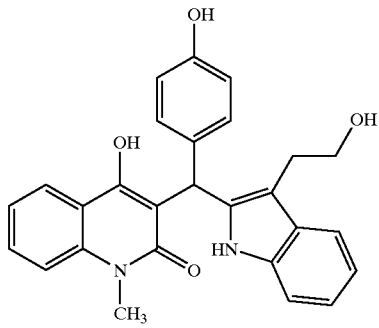

(IV)

or a pharmaceutically acceptable salt thereof.

6. A compound according to claim 1, which is SF2809-V substance represented by the following formula (V)

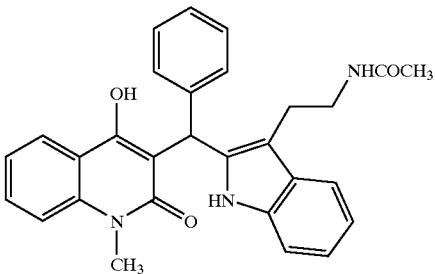

(V)

or a pharmaceutically acceptable salt thereof.

7. A compound according to claim 1, which is SF2809-VI substance represented by the following formula (VI)

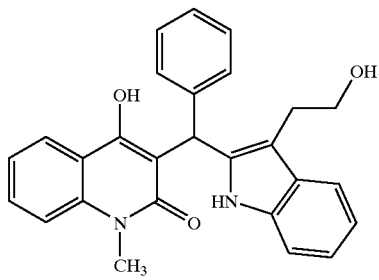

(VI)

or a pharmaceutically acceptable salt thereof.

8. A process for the production of at least one of SF2809-I substance, SF2809-II substance, SF2809-III substance, SF2809-IV substance, SF2809-V substance and SF2809-VI substance each represented by the following formula (VII)

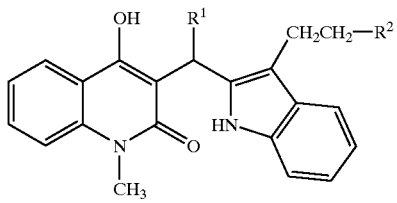

(VII)

wherein R$^1$ is a hydrogen atom, phenyl group or p-hydroxyphenyl group, and R$^2$ is acetylamino group —NHCOCH$_3$ or hydroxyl group, and wherein R$^1$ is hydrogen atom and $R^2$ is acetylamino group for SF2809-I substance; $R^1$ is p-hydroxyphenyl group and $R^2$ is acetylamino group for SF2809-II substance; $R^1$ is hydrogen atom and $R^2$ is hydroxyl group for SF2809-III substance; $R^1$ is p-hydroxyphenyl group and $R^2$ is hydroxyl group for SF2809-IV substance; $R^1$ is phenyl group and $R^2$ is acetylamino group for SF2809-V substance; and $R^1$ is phenyl group and $R^2$ is hydroxyl group for SF2809-VI substance, or a pharmaceutically acceptable salt thereof, the process comprising cultivating a microbial strain which belongs to the genus Dactylosporangium and which produces at least one of SF2809-I substance of formula (I), SF2809-II substance of formula (II), SF2809-III substance of formula (III), SF2809-IV substance of formula (IV), SF2809-V substance of formula (V) and SF2809-VI substance of formula (VI) as claimed in claim 1, and then recovering from the resulting culture at least one of the SF2809-I substance, SF2809-II substance, SF2809-III substance, SF2809-IV substance, SF2809-V substance and SF2809-VI substance.

9. A process according to claim 8, wherein the microbial strain to be used for producing at least one of the SF2809-I to SF2809-VI substances is the strain SF2809 contained in deposited strain FERM BP-6872.

10. A pharmaceutical composition which comprises as an active ingredient SF2809-I substance of formula (I), SF2809-II substance of formula (II), SF2809-III substance of formula (III), SF2809-IV substance of formula (IV), SF2809-V substance of formula (V) or SF2809-VI substance of formula (VI) or a pharmaceutically acceptable salt thereof as claimed in claim 1, in combination with a pharmaceutically acceptable carrier.

11. A pharmaceutical composition according to claim 10, which is for use in the therapy or prevention of cardiac infarction, cardiomegaly, cardiac insufficiency, myocardosis, arteriosclerosis, hypertension, hemangioendotyrosis, peripheral cardiovascular disorder, renal insufficiency, inflammations, allergy, atopic dermatitis, rheumatism, asthma or bronchitis.

12. A chymase inhibitor consisting of SF2809-I substance of formula (I), SF2809-II substance of formula (II), SF2809-III substance of formula (III), SF2809-IV substance of formula (IV), SF2809-V substance of formula (V) or SF2809-VI substance of formula (VI) or a pharmaceutically acceptable salt thereof as claimed in claim 1.

13. Strain SF2809, which microorganism has microbiological properties described in the specification and which belongs to the genus Dactylosporangium, and has such characteristic that it is capable of producing the SF2809-I substance of formula (I), SF2809-II substance of formula (II), SF2809-III substance of formula (III), SF2809-IV substance of formula (IV), SF2809-V substance of formula (V) and SF2809-VI substance of formula (VI) as claimed in claim 1, and which strain SF2809 contained in deposited strain FERM BP-6872.

* * * * *